(12) United States Patent
Long

(10) Patent No.: US 8,557,734 B2
(45) Date of Patent: Oct. 15, 2013

(54) HERBICIDAL COMPOSITIONS

(75) Inventor: David A. Long, Lee's Summit, MO (US)

(73) Assignee: Bayer CropScience LP, Research Triangle Park, NC (US)

( * ) Notice: Subject to any disclaimer, the term of this patent is extended or adjusted under 35 U.S.C. 154(b) by 1008 days.

(21) Appl. No.: 11/097,902

(22) Filed: Apr. 1, 2005

(65) Prior Publication Data

US 2005/0221993 A1 Oct. 6, 2005

Related U.S. Application Data

(60) Provisional application No. 60/559,757, filed on Apr. 6, 2004.

(51) Int. Cl.
*A01N 25/02* (2006.01)
*A01N 47/00* (2006.01)
*A01N 47/08* (2006.01)
*A01N 43/00* (2006.01)

(52) U.S. Cl.
USPC ............... 504/116.1; 504/143; 514/245

(58) Field of Classification Search
USPC ................. 504/116.1, 143; 514/245
See application file for complete search history.

(56) References Cited

U.S. PATENT DOCUMENTS

| | | | | |
|---|---|---|---|---|
| 5,246,912 A * | 9/1993 | Nielsen | ............ | 504/135 |
| 5,264,411 A * | 11/1993 | Hewett et al. | ............ | 504/130 |
| 5,888,934 A * | 3/1999 | Townson et al. | ............ | 504/206 |
| 6,461,997 B1 * | 10/2002 | Hegde et al. | ............ | 504/273 |
| 6,627,595 B2 * | 9/2003 | Wurtz et al. | ............ | 510/422 |
| 6,746,988 B2 * | 6/2004 | Hopkinson et al. | ............ | 504/127 |
| 6,946,426 B2 * | 9/2005 | Martin et al. | ............ | 504/139 |
| 2003/0060496 A1 * | 3/2003 | Merritt et al. | ............ | 514/383 |

FOREIGN PATENT DOCUMENTS

CA 2366645 A1 * 3/2000

* cited by examiner

*Primary Examiner* — Fereydoun G Sajjadi
*Assistant Examiner* — Courtney Brown

(57) ABSTRACT

This invention relates to a new herbicidal composition comprising desmedipham and optionally phenmedipham and/or ethofumesate.

18 Claims, No Drawings

HERBICIDAL COMPOSITIONS

BACKGROUND OF THE INVENTION

The present invention provides new herbicidal compositions.

It is known to apply the herbicidal active ingredients desmedipham, phenmedipham and ethofumesate alone or combined with one another. It is further known that these herbicides are generally difficult to formulate alone or in combination in agriculturally acceptable compositions that provide (a) agriculturally acceptable emulsions when diluted in water and (b) before dilution into water, in a maximum concentration that minimizes precipitation of the active ingredients. These properties have been particularly difficult to achieve as the compositions are often subjected to harsh storage conditions (e.g., large variations in temperature, pressure and humidity) for up to 2 years.

An object of the present invention is to provide new herbicidal compositions comprising desmedipham and optionally, phenmedipham and/or ethofumesate that solve the above-mentioned problems.

Another object of the present invention is to provide new herbicidal compositions comprising desmedipham and optionally phenmedipham and/or ethofumesate that provide greater safety to crops and excellent herbicidal action when appropriately applied.

Another object of the present invention is to provide new herbicidal compositions comprising desmedipham and/or phenmedipham and/or ethofumesate that provide agriculturally acceptable emulsions when diluted into water.

The objects of the present invention are met in whole or in part by the present invention.

SUMMARY OF THE INVENTION

The present invention provides a herbicidal composition comprising:
(a) from about 5% to 40% by weight of desmedipham;
(b) from about 10% to 20% by weight of N-methylpyrrolidone;
(c) from about 20% to 40% by weight of a hydrophobic aromatic solvent comprising aromatic hydrocarbons from about $C_9$ to $C_{16}$ and having a boiling range of from about 165° C. to about 290° C.;
(d) from about 5% to 15% by weight of a surfactant which is a mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
(e) from about 2% to 15% of one or more non-ionic surfactants having an average hydrophilic-lypophilic balance (HLB) value of from about 5 to 15.

DETAILED DESCRIPTION OF THE INVENTION

Unless specifically stated otherwise in the present description and accompanying claims, the amounts of ingredients in the compositions of the invention are by percent by weight. Unless specifically stated otherwise in the present description and claims, the word "about" describing a range refers to both the lesser and the greater numbers.

Preferably, component (e) comprises two or more non-ionic surfactants. When two or more non-ionic surfactants are used, the HLB value is an average value of the two or more individual HLB values of the individual non-ionic surfactants. Preferably the HLB value is from about 10 to 15, more preferably from 12 to 14.

In an embodiment, component (e) comprises from about 2% to 15% of one or more, preferably two or more, polyethoxylated alcohols wherein (i) the alcohol portion is a $C_8$-$C_{20}$ alcohol and (ii) the polyethoxylated portion averages, per mole of alcohol, from about 2 to 5 moles of ethoxy groups; or greater than about 6 to 9 moles of ethoxy groups; or greater than about 10 to 13 moles of ethoxy groups; or greater than about 14 to 16 moles of ethoxy groups; or greater than about 17 to 20 moles of ethoxy groups; or greater than about 21 to 25 moles of ethoxy groups.

In another embodiment, the polyethoxylated alcohols have an alcohol portion which is a $C_{10}$-$C_{16}$ alcohol, preferably a $C_{12}$-$C_{15}$ alcohol.

In another embodiment, the present invention provides a composition comprising:
(a) from about 25% to 40% by weight of desmedipham;
(b) from about 15% to 20% by weight of N-methylpyrrolidone;
(c) from about 25% to 35% by weight of a hydrophobic aromatic solvent comprising aromatic hydrocarbons from about $C_9$ to $C_{16}$ and having a boiling range of from about 165° C. to about 290° C.;
(d) from about 5% to 15% by weight of a surfactant comprising a mixture of monohydrogen and dihydrogen phosphate esters of α-[2,4,6-tris[1-(phenyl)-ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
(e1) from about 3% to 9% of a first polyethoxylated alcohol wherein the alcohol is a $C_{12}$-$C_{15}$ alcohol and the polyethoxylated portion averages about 4 moles of ethoxy groups per mole of alcohol; and
(e2) from about 2% to 4% of a second polyethoxylated alcohol wherein the alcohol is a $C_{12}$-$C_{15}$ alcohol and the polyethoxylated portion averages about 20 moles of ethoxy groups per mole of alcohol.

Desmedipham is preferably provided in an amount from about 28% to 35%, more preferably from about 29% to 32%.

N-methylpyrrolidone is preferably provided in an amount from about 17% to 19%.

The solvent is preferably provided in an amount from about 28% to 33%, more preferably from 30% to 32%.

The surfactant is preferably provided in an amount from about 7% to 12%, more preferably from about 9% to 11%.

The first polyethoxylated alcohol is preferably provided in an amount from about 4% to 8%, more preferably from 5% to 8%.

The second polyethoxylated alcohol is preferably provided in an amount from about 2% to 3.5%, more preferably from 2.5% to 3.5%.

The present invention also provides a herbicidal composition comprising:
(a) from about 12% to 18% by weight of desmedipham;
(b) from about 12% to 18% by weight of phenmedipham;
(c) from about 15% to 20% by weight of N-methylpyrrolidone;
(d) from about 25% to 35% by weight of a hydrophobic aromatic solvent comprising aromatic hydrocarbons from about $C_9$ to $C_{16}$ and having a boiling range of from about 165° C. to about 290° C.;
(e) from about 5% to 15% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;

(f) from about 3% to 9% of a first polyethoxylated alcohol wherein the alcohol is a $C_{12}$-$C_{15}$ alcohol and the polyethoxylated portion averages about 4 moles of ethoxy groups per mole of alcohol; and (g) from about 2% to 4% of a first polyethoxylated alcohol wherein the alcohol is a $C_{12}$-$C_{15}$ alcohol and the polyethoxylated portion averages about 20 moles of ethoxy groups per mole of alcohol.

Desmedipham is preferably provided in an amount from about 13% to 17%, more preferably from about 14% to 16%.

Phenmedipham is preferably provided in an amount from about 13% to 17%, more preferably from about 14% to 16%.

N-methylpyrrolidone is preferably provided in an amount from about 17% to 19%.

The solvent is preferably provided in an amount from about 28% to 33%, more preferably from 30% to 32%.

The surfactant is preferably provided in an amount from about 7% to 12%, more preferably from about 9% to 11%.

The first polyethoxylated alcohol is preferably provided in an amount from about 4% to 8%, more preferably from 5% to 8%.

The second polyethoxylated alcohol is preferably provided in an amount from about 2% to 3.5%, more preferably from 2.5% to 3.5%.

The present invention also provides an herbicidal composition comprising:

(a) from about 5% to 15% by weight of desmedipham;
(b) from about 10% to 20% by weight of phenmedipham;
(c) from about 12% to 18% by weight of ethofumesate;
(d) from about 15% to 20% by weight of N-methylpyrrolidone;
(e) from about 25% to 35% by weight of a hydrophobic aromatic solvent comprising aromatic hydrocarbons from about $C_9$ to $C_{16}$ and having a boiling range of from about 165° C. to about 290° C.;
(f) from about 5% to 15% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
(g) from about 3% to 9% of a first polyethoxylated alcohol wherein the alcohol is a $C_{12}$-$C_{15}$ alcohol and the polyethoxylated portion averages about 4 moles of ethoxy groups per mole of alcohol; and
(h) from about 2% to 4% of a second polyethoxylated alcohol wherein the alcohol is a $C_{12}$-$C_{15}$ alcohol and the polyethoxylated portion averages about 20 moles of ethoxy groups per mole of alcohol.

Desmedipham is preferably provided in an amount from about 13% to 17%, more preferably from about 14% to 16%.

Phenmedipham is preferably provided in an amount from about 13% to 17%, more preferably from about 14% to 16%.

Ethofumesate is preferably provided in an amount from about 12% to 18%, more preferably from about 13% to 17%, most preferably from about 15% to 17%.

N-methylpyrrolidone is preferably provided in an amount from about 17% to 19%.

The solvent is preferably provided in an amount from about 28% to 33%, more preferably from 30% to 32%.

The surfactant is preferably provided in an amount from about 7% to 12%, more preferably from about 9% to 11%.

The first polyethoxylated alcohol is preferably provided in an amount from about 4% to 8%, more preferably from 4% to 6%.

The second polyethoxylated alcohol is preferably provided in an amount from about 4% to 8%, more preferably from 4% to 6%.

The solvent of the invention is substantially free of isophorone. By the term substantially free is meant less than 0.5%, preferably less than 0.1% of isophorone.

The solvent is generally comprises one or more aromatic hydrocarbons having a boiling point of from about 150° C. to 300° C. The component or the components of the solvent are substantially immiscible in water. Generally the miscibility is about or less than 0.01 g/100 grams water at 25° C.

The compositions of the invention are emulsion concentrates that are improved over those of the prior art. When diluted into water, the emulsion concentrates provide stable emulsions that, when sprayed, have improved attributes over those diluted emulsion concentrates of the prior art.

EXAMPLE

The following compounds were used in the Example:

Aromatic 200 Solvent naphtha, Heavy Aromatic C9-16 330F-554F, a complex combination of hydrocarbons obtained from the distillation of aromatic streams and consisting predominantly of aromatic hydrocarbons having carbon numbers predominantly in the range of C9 through C16 and boiling in the range of approximately 165° C. to 290° C. (330° F. to 554° F.) (from ExxonMobil Chemical Company)

Soprophor D33LN α-[2,4,6-Tris[1-(phenyl)ethyl]phenyl ω-hydroxy poly(oxyethylene); mixture of monohydrogen and dihydrogen phosphate esters, the poly(oxyethylene) content averages 16 moles (from Rhodia)

Synperonic A20 Ethoxylated Fatty Alcohol; Polyoxyethylene (20) C12-C15 alcohols with an average of 20 moles of ethylene oxide having an HLB of 16 (from Uniqema, an international business of Imperial Chemical Industries PLC)

Synperonic A4 Ethoxylated Fatty Alcohol; Polyoxyethylene (4) C12-$C_{15}$ alcohols with an average of 4 moles of ethylene oxide having an HLB of 9 (from Uniqema)

A mixture of N-methylpyrrolidone (Agsolex 1, ISP—International Specialty Products) and Aromatic 200 is heated to about 55° C. while stirring. The active ingredients desmedipham, phenmedipham and ethofumesate (Bayer CropScience LP, Research Triangle Park, N.C., USA) are added as needed. Heating and stirring are maintained until substantially no solids are visible. Following partial cooling and while the solution is warm to the touch, that is approximately 40° C., Synperonic A20 is added and dissolved. The solution is gradually cooled to about 25° C. and the remaining surfactants Soprophor 3D33 LN and Synperonic A4 are added and the solution is stirred until uniform.

The mixture is filtered through a 5 micron (μm) screen or a packed clay filter which filtering agent is diatomaceous earth. The resulting solution is then ready for packaging and use in the field. A sample of the composition prepared is tested for the content of the active ingredients. A sample of the composition is diluted into water to confirm the quality of the emulsion so formed.

Compositions of the invention prepared according to the above procedure provide generally predictable amounts of active ingredients in the compositions and agriculturally acceptable emulsions when diluted into water in preparation for application to a crop locus.

The following table provides representative mixtures of the invention. Numbers are given in grams and the total is 100 g of each composition.

| Ingredient | Composition A | Composition B | Composition C |
| --- | --- | --- | --- |
| Desmedipham 98.6% | 10.35 | 15.21 | 30.43 |
| Phenmedipham 99.1% | 13.23 | 15.14 | — |
| Ethofumesate 97.6% | 16.26 | — | — |
| Agsolex 1 | 16.20 | 18.40 | 18.40 |
| Aromatic 200 | 24.96 | 31.25 | 31.17 |
| Soprophor D33LN | 9.8 | 10 | 10 |
| Synperonic A4 | 4.6 | 7 | 7 |
| Synperonic A20 | 4.6 | 3 | 3 |

What is claimed is:

1. A herbicidal composition comprising:
   (a) from about 5% to 40% by weight of desmedipham;
   (b) from about 10% to 20% by weight of N-methylpyrrolidone;
   (c) from about 20% to 40% by weight of a hydrophobic aromatic solvent comprising aromatic hydrocarbons from about C9 to C16 and having a boiling range of from about 165° C. to about 290° C.;
   (d) from about 5% to 15% by weight of a surfactant which is a mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion; and
   (e) from about 2% to 15% of one or more surfactants, wherein said one or more surfactants is a polyoxyethylene C12-C15 alcohol having an average hydrophilic-lypophilic balance value of from about 5 to 15.

2. The herbicidal composition of claim 1 comprising:
   (a) from about 25% to 40% by weight of desmedipham;
   (b) from about 15% to 20% by weight of N-methylpyrrolidone;
   (c) from about 25% to 35% by weight of a hydrophobic aromatic solvent comprising aromatic hydrocarbons from about C9 to C16 and having a boiling range of from about 165° C. to about 290° C.;
   (d) from about 5% to 15% by weight of a surfactant which is a mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
   (e1) from about 3% to 9% of a first polyethoxylated alcohol wherein the alcohol is a C12-C15 alcohol and the polyethoxylated portion averages about 4 moles of ethoxy groups per mole of alcohol; and
   (e2) from about 2% to 4% of a second polyethoxylated alcohol wherein the alcohol is a C12-C15 alcohol and the polyethoxylated portion averages about 20 moles of ethoxy groups per mole of alcohol.

3. A herbicidal composition comprising:
   (a) from about 12% to 18% by weight of desmedipham;
   (b) from about 12% to 18% by weight of phenmedipham;
   (c) from about 15% to 20% by weight of N-methylpyrrolidone;
   (d) from about 25% to 35% by weight of a hydrophobic aromatic solvent comprising aromatic hydrocarbons from about C9 to C16 and having a boiling range of from about 165° C. to about 290° C.;
   (e) from about 5% to 15% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
   (f) from about 3% to 9% of a first polyethoxylated alcohol wherein the alcohol is a C12-C15 alcohol and the polyethoxylated portion averages about 4 moles of ethoxy groups per mole of alcohol; and
   (g) from about 2% to 4% of a second polyethoxylated alcohol wherein the alcohol is a C12-C15 alcohol and the polyethoxylated portion averages about 20 moles of ethoxy groups per mole of alcohol.

4. A herbicidal composition comprising:
   (a) from about 5% to 15% by weight of desmedipham;
   (b) from about 10% to 20% by weight of phenmedipham;
   (c) from about 12% to 18% by weight of ethofumesate;
   (d) from about 15% to 20% by weight of N-methylpyrrolidone;
   (e) from about 25% to 35% by weight of a hydrophobic aromatic solvent comprising aromatic hydrocarbons from about C9 to C16 and having a boiling range of from about 165° C. to about 290° C.;
   (f) from about 5% to 15% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
   (g) from about 3% to 9% of a first polyethoxylated alcohol wherein the alcohol is a C12-C15 alcohol and the polyethoxylated portion averages about 4 moles of ethoxy groups per mole of alcohol; and
   (h) from about 2% to 4% of a second polyethoxylated alcohol wherein the alcohol is a C12-C15 alcohol and the polyethoxylated portion averages about 20 moles of ethoxy groups per mole of alcohol.

5. The herbicidal composition of claim 1, wherein component (e) comprises two or more non-ionic surfactants.

6. The herbicidal composition of claim 1, wherein said herbicidal composition forms a stable emulsion when diluted in water.

7. The herbicidal composition of claim 2, wherein component (e1) exhibits a hydrophilic-lypophilic balance value of about 9.

8. The herbicidal composition of claim 2, wherein component (e2) exhibits a hydrophilic-lypophilic balance value of about 16.

9. The herbicidal composition of claim 1, wherein said herbicidal composition comprises from about 5% to 15% by weight of desmedipham.

10. The herbicidal composition of claim 1, wherein said herbicidal composition comprises from about 13% to 17% by weight of desmedipham.

11. The herbicidal composition of claim 4, wherein said herbicidal composition comprises from about 13% to 17% by weight of phenmedipham.

12. The herbicidal composition of claim 4, wherein said herbicidal composition comprises from about 13% to 17% by weight of ethofumesate.

13. The herbicidal composition of claim 1 comprising:
   (a) about 30% by weight of desmedipham;
   (b) about 18% by weight of N-methylpyrrolidone;
   (c) about 31% by weight of a hydrophobic aromatic solvent comprising aromatic hydrocarbons from about C9 to C16 and having a boiling range of from about 165° C. to about 290° C.;

(d) about 10% by weight of a surfactant which is a mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;

(e1) about 7% of a first polyethoxylated alcohol wherein the alcohol is a C12-C15 alcohol and the polyethoxylated portion averages about 4 moles of ethoxy groups per mole of alcohol; and (e2) about 3% of a second polyethoxylated alcohol wherein the alcohol is a C12-C15 alcohol and the polyethoxylated portion averages about 20 moles of ethoxy groups per mole of alcohol.

14. A herbicidal composition comprising:
(a) about 15% by weight of desmedipham;
(b) about 15% by weight of phenmedipham;
(c) about 18% by weight of N-methylpyrrolidone;
(d) about 31% by weight of a hydrophobic aromatic solvent comprising aromatic hydrocarbons from about C9 to C16 and having a boiling range of from about 165° C. to about 290° C.;
(e) about 10% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
(f) about 7% of a first polyethoxylated alcohol wherein the alcohol is a C12-C15 alcohol and the polyethoxylated portion averages about 4 moles of ethoxy groups per mole of alcohol; and
(g) about 3% of a second polyethoxylated alcohol wherein the alcohol is a C12-C15 alcohol and the polyethoxylated portion averages about 20 moles of ethoxy groups per mole of alcohol.

15. A herbicidal composition comprising:
(a) about 10% by weight of desmedipham;
(b) about 13% by weight of phenmedipham;
(c) about 16% by weight of ethofumesate;
(d) about 16% by weight of N-methylpyrrolidone;
(e) about 25% by weight of a hydrophobic aromatic solvent comprising aromatic hydrocarbons from about C9 to C16 and having a boiling range of from about 165° C. to about 290° C.;
(f) about 10% by weight of a surfactant which is mixture of monohydrogen and dihydrogen phosphate esters of α-[2,4,6-tris[1-(phenyl)ethyl]phenyl ω-hydroxy poly(oxyethylene) wherein the poly(oxyethylene) portion averages about 16 moles per mole of the α-[2,4,6-tris[1-(phenyl)ethyl]phenyl ω-hydroxy portion;
(g) about 5% of a first polyethoxylated alcohol wherein the alcohol is a C12-C15 alcohol and the polyethoxylated portion averages about 4 moles of ethoxy groups per mole of alcohol; and
(h) about 5% of a second polyethoxylated alcohol wherein the alcohol is a C12-C15 alcohol and the polyethoxylated portion averages about 20 moles of ethoxy groups per mole of alcohol.

16. An emulsion concentrate comprising the herbicidal composition of claim 1, wherein said emulsion concentrate is stable when diluted in water.

17. An emulsion concentrate comprising the herbicidal composition of claim 3, wherein said emulsion concentrate is stable when diluted in water.

18. An emulsion concentrate comprising the herbicidal composition of claim 4, wherein said emulsion concentrate is stable when diluted in water.

* * * * *